United States Patent [19]

Ferreira et al.

[11] Patent Number: 4,702,259

[45] Date of Patent: Oct. 27, 1987

[54] DEVICE FOR MEASURING AND INDICATING CHANGES IN RESISTANCE OF A LIVING BODY

[75] Inventors: Marc Ferreira, Los Angeles; John McCormick, Grass Valley; Raymond Bernard, Los Angeles; Joseph Butryn, Los Angeles; Ronald Clifford, Los Angeles, all of Calif.

[73] Assignee: Author's Family Trust, Los Angeles, Calif.

[21] Appl. No.: 903,698

[22] Filed: Sep. 4, 1986

Related U.S. Application Data

[63] Continuation-in-part of Ser. No. 773,348, Sep. 6, 1985, abandoned.

[51] Int. Cl.[4] .............................................. A61B 5/05
[52] U.S. Cl. ................................................... 128/734
[58] Field of Search ............... 128/735, 734, 690, 693, 128/689

[56] References Cited

U.S. PATENT DOCUMENTS

| | | | |
|---|---|---|---|
| 3,290,589 | 12/1966 | Hubbard | 346/62 R |
| 3,924,606 | 12/1975 | Silva et al. | 128/734 |
| 3,949,736 | 4/1976 | Vrann et al. | 128/734 |
| 3,971,365 | 7/1976 | Smith | 128/734 |
| 4,182,314 | 1/1980 | Boughton | 128/734 |
| 4,459,995 | 7/1984 | Conners et al. | 128/734 |

Primary Examiner—Edward M. Coven
Attorney, Agent, or Firm—Koda and Androlia

[57] ABSTRACT

A device for measuring and indicating changes in the resistance of a living body including an analog portion, a digital portion and a source of power for supplying stable power to the analog and digital portions. The analog portion includes a bridge network which includes a potentiometer for setting a reference level for the device. The digital portion includes a potentiometer which turns together with the potentiometer provided in the analog portion and digital processing circuitry and digital displays for determining and displaying a count indicative of the position of the potentiometer and the total amount of rotation of said potentiometer. In addition, a computer could be interfaced with the device to record or play back the changes in the resistance of the living body.

7 Claims, 3 Drawing Figures

DEVICE FOR MEASURING AND INDICATING CHANGES IN RESISTANCE OF A LIVING BODY

This is a continuation-in-part application of Ser. No. 773,348, filed Sept. 6, 1985 now abandoned.

BACKGROUND OF THE INVENTION

1. Field of the Invention

This invention relates to devices for indicating variations in electrical resistance of living bodies and more particularly, human bodies.

2. Prior Art

In the prior art there exist devices for measuring resistance of a living body. Such devices are sometimes referred to as galvonic skin response (GSR) devices and are used in a variety of applications. Such applications include polygraphs and research uses. Examples of such prior art devices are shown in U.S. Pat. No. 3,290,589, U.S. Pat. No. 4,459,995 and U.S. Pat. No. 4,300,574.

Such instruments contained in the prior art have several drawbacks. Firstly, the better instruments have a high power consumption, are very expensive, are very complex, are large and non-portable and have complex and confusing controls. The less expensive and portable units also have other disadvantages. In particular, such disadvantages include high power consumption, poor stability, low sensitivity and an expensive and complex power source. In addition, such more expensive and less expensive devices share certain common disadvantages. In particular, the circuitry is typically noisy, it is difficult to accurately read the position of the controls, it is difficult to maintain stable voltages and no provision is provided for the operator to instantaneously check to determine if the variations in the output readings are the result of changes in the living body or some failure in the equipment without recalibrating the entire device.

SUMMARY OF THE INVENTION

Accordingly, it is a general object of the present invention to provide a device for measuring and indicating changes in the resistance of a living body which has low power consumption, high stability, portability, high sensitivity, low noise, simple controls, a single battery source, an accurate display of the position of the controls and a means for instantaneously determining if the fluctuations in the readings are the result of the equipment or the living body being measured.

In keeping with the principles of the present, invention the objects are accomplished by a unique device for measuring and indicating changes in resistance of a living body. The device generally includes an analog portion, a digital portion and a power supply portion which supplies a stable source of power to both the digital and the analog portions and which utilizes a single battery source. The analog portion generally includes a bridge network which is coupled to a transistorized amplifier whose output is connected to a meter movement. The digital portion generally includes digital circuitry and displays for accurately determining and displaying the position of the important controls.

BRIEF DESCRIPTION OF THE DRAWINGS

The above mentioned features and objects of the present invention will become more apparent in relation to the following description taken in conjunction with the following drawings wherein like reference numerals denote like elements and in which.

DETAILED DESCRIPTION OF THE INVENTION

Figure 1:
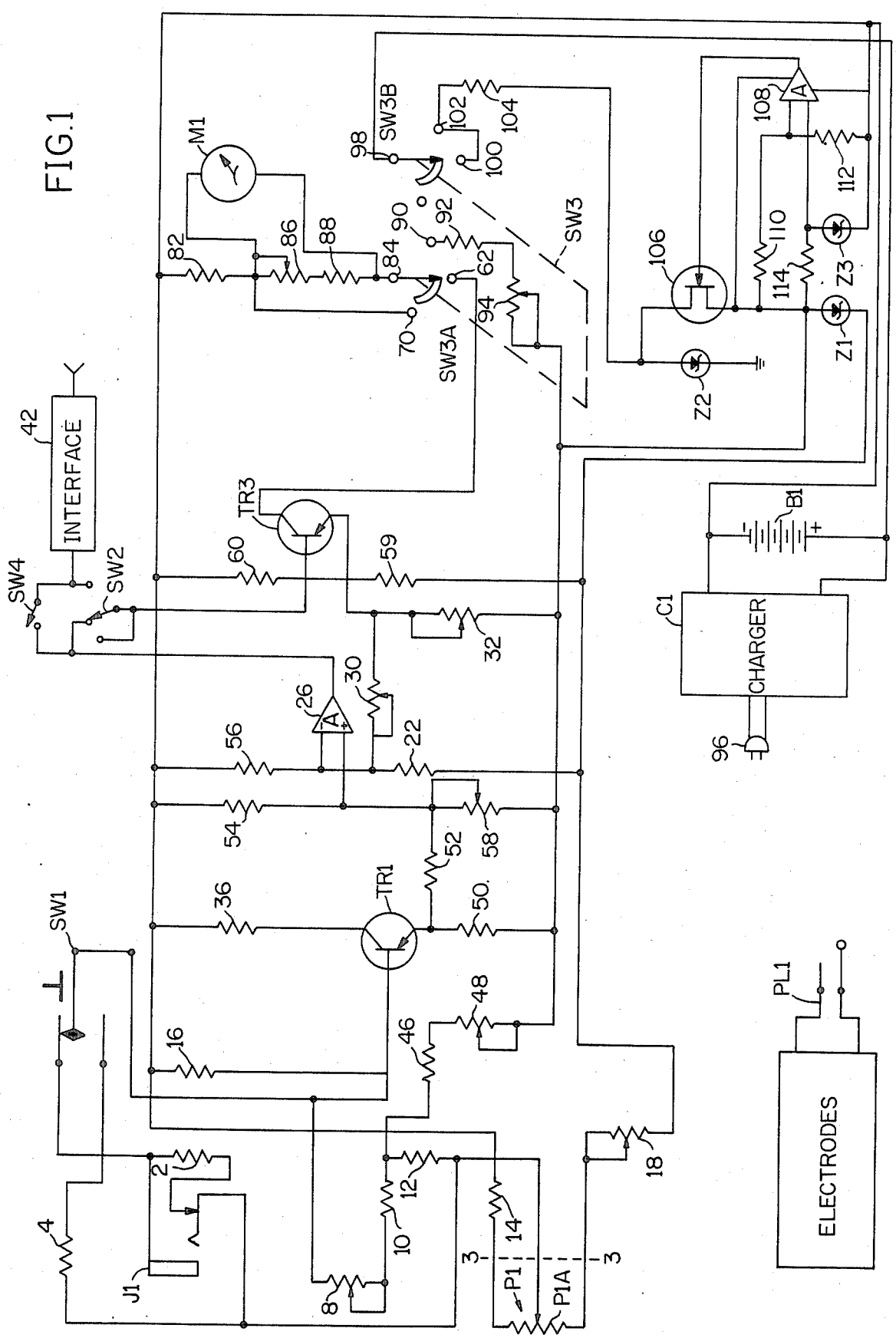
FIG. 1 is a circuit diagram of the analog portion of the device.

Referring to FIG. 1, shown therein is a circuit diagram of the analog portion of a device for measuring and indicating the resistance of a living body in accordance with the teachings of the present invention. In FIG. 1 the device includes an ungrounded normally closed jack J1. Across the jack J1 is connected in parallel a resistor 2. The resistor 2 is coupled to the normally closed jack J1 such that when a plug is inserted into the jack J1, the resistor 2 is disconnected from across the jack J1. The collar of jack J1 is further connected to the normally closed contact of switch SW1. Switch SW1 is a push button switch and the movable contact of the push button switch SW1 is connected to the base of transistor TR1. The other normally opened contact of push button switch SW1 is connected to the tip of jack J1 via resistor 4.

The base of the transistor TR1 is further connected to a variable resistor 8. The other side of the variable resistor 8 is connected back to the tip of jack J1 through the series connection of resistor 10 and resistor 12. The tip of jack J1 is also connected to the wiper of potentiometer section P1A of ganged potentiometer P1. One terminal of potentiometer section P1A is connected to the base of transistor TR1 via the series connection of resistors 14 and 16. The other terminal of potentiometer section P1A is connected to the minus input of operational amplifier 26 via the series connection of resistor 18 and resistor 22. The connection point between resistor 18 and the resistor 22 is further connected to the anode of zenor diode Z1.

The side of resistor 16 oppositely connected from the base of transistor TR1 and the collector of transistor TR1 are both connected together via resistor 36 and are connected to a negative terminal of the battery B1. The connection point between resistors 10 and 12 is further connected to the cathode of zenor diode Z1 via the series connection of fixed resistor 46 and variable resistor 48. The emitter of transistor TR1 is connected respectively to the cathode of zenor diode Z1 via resistor 50 and to the plus input of operational amplifier 26 via resistor 52.

The plug input of amplifier 26 is connected to the negative terminal of battery B1 via resistor 54 and the minus input of amplifier 26 is also connected to the negative terminal of battery B1 via resistor 56. The plus input of amplifier 26 is connected via variable resistor 58 to the cathode of zenor diode Z1. The output of amplifier 26 is further connected via switch SW2 to the base of transistor TR3. The base of transistor TR3 is further connected respectively to the anode of zenor diode Z1 via resistor 59 and to the negative terminal of battery B1 via resistor 60. The collector of transistor TR3 is connected to contact 62 of switch section SW3A of switch SW3.

The minus input of amplifier 26 is further connected to the emitter of transistor TR3 via resistor 30. Also, the emitter of transistor TR3 is connected to the cathode of zenor diode Z1 via variable resistor 32.

Contacts 64, 66 and 68 of switch section SW2B are connected to contact 70 of switch SW3A via respectively resistors 72. 74 and the series connection of resistors 76 and 78. Switch contact 80 of switch SW2B is connected to the point where resistors 76 and 80 are connected together.

Switch contact 70 is further connected respectively to the negative terminal of meter M1, the negative side of battery B1 via resistor 82 and to contact 84 of switch section SW3A via variable resistor 86 and fixed resistor 88. Contact 84 is further connected to the plus terminal of meter M1. Switch contact 90 of switch section SW3B is connected to the cathode of zenor diode Z1 via fixed resistor 92 and variable resistor 94.

The base of transistor TR3 is connected to the fixed switch contact of switch SW2. The remaining contact of switch SW2 is connected to the computer interface 42. Also, the output of operational amplifier 26 is connected to the computer interface 42 via switch SW4.

A charger C1 for charging the battery B1 is connected across the battery B1 and also powered via a power cord and plug 96. The positive side of the battery B1 is connected to switch contact 98 of switch section SW3B. Contact 100 of switch section SW3B is connected to switch contact 102 and further to the anode of zenor diode Z2 via resistor 104. The cathode of zenor diode Z2 is connected to the ground and the anode of zenor diode Z2 is connected to the source of MOSFET 106. The drain of MOSFET 106 is connected to the cathode of zenor diode Z1. The gate of MOSFET 106 is connected to and controlled by the output of operational amplifier 108.

The drain of MOSFET 106 is further connected to the positive power terminal of operational amplifier 108 and to one input of the operational amplifier 108 via resistor 110. This same input of the operational amplifier 108 is connected to the negative terminal of battery B1 via resistor 112. The negative power terminal of operational amplifier 108 is connected to the negative terminal of battery B1. Furthermore, the other input of the operational amplifier 108 is connected to the cathode of zenor diode Z3 and the anode of zenor diode Z3 is connected to the negative terminal of battery B1. The cathodes of zenor diodes Z1 and Z3 are coupled together via resistor 114.

Figure 2:
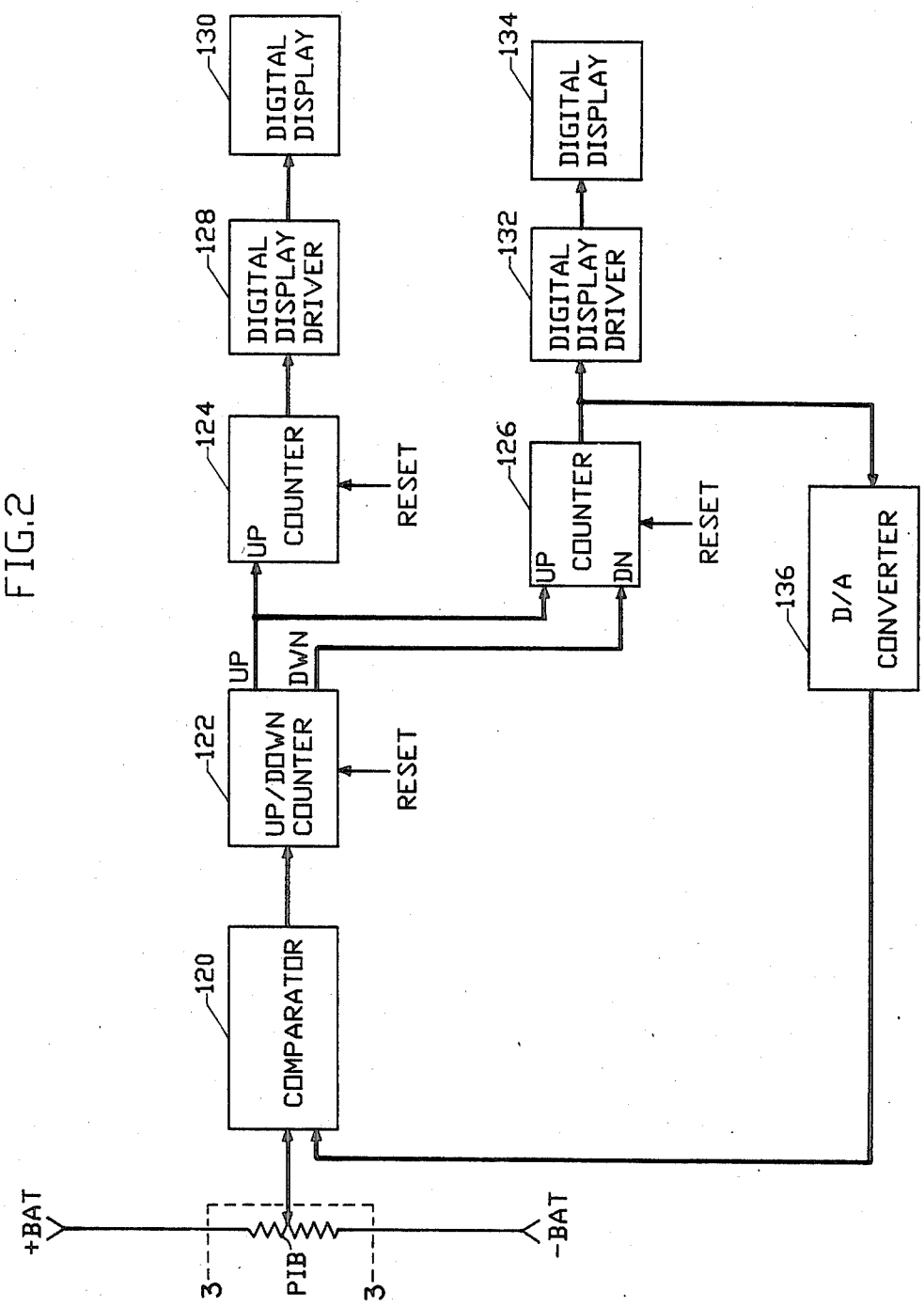
FIG. 2 is a diagram of the digital portion of the device.

Now referring to the digital section shown in FIG. 2. the digital portion comprises a potentiometer section P1B which is the other half of the ganged potentiometer P1 and turns in unison with potentiometer P1A which is provided in the analog section. The battery B1 is connected across the potentiometer section P1B and the movable contact of the potentiometer section P1B is connected to the input of a comparator 120. The output of the comparator 120 is a positive signal if the input from the potentiometer section P1B is greater than the signal to be compared, a minus if the output voltage from the potentiometer section P1B is less than the reference to be compared with and a zero if they are equal. The output of comparator 120 is supplied to an UP/DOWN counter 122. The UP/DOWN counter counts up with the application of a positive signal and counts down with the application of a negative signal. The up count of UP/DOWN counter 122 is connected to the up count inputs of counters 124 and 126. The down count output of counter 122 is connected only to the down count input of counter 126. The output of counter 124 is connected to a digital display driver 128 and digital display drive 128 derives a digital display 130. The digital display 130 can be any type of digital display, but preferably it should a liquid crystal display type because of the low power consumption.

The output of counter 126 is connected to the input of a digital display driver 132 which drives a second digital display 134. Again, the digital display 134 can be any type or digital display, but is preferably a liquid crystal display type because of the low power consumption.

The output of counter 126 is further supplied to a digital to analog converter 136. The output of the digital to analog converter 136 is connected to the other input of comparator 120 and provides the feedback comparison signal for the comparator 120.

It should be apparent to one skilled in the art that the operation of the digital portion is controlled by a clock signal (not shown) in a manner well known in the art. In addition, as is also well known in the art, the clock signal can be used by the counters 122, 124 and 126 to perform their counting.

Referring to FIGS. 1 and 2, in operation the device is turned on utilizing the switch SW3. Next the electrodes are connected to the device by inserting the plug PL1 into the jack J1 and a living body is connected to the electrodes. The electrodes are then part of the bridge network and the bridge is initially balanced utilizing variable resistor 8. The transistors TR1 and TR3 together with operational amplifier 26 form transistor amplifier which amplifies the variations in the balance of the bridge network caused by changes in the resistance of the living body. To keep the noise as low as possible in the transistor amplifier, silicon type transistors are utilized instead of germanium. Variable resistor 30 is utilized to set the needle of the M1 within the range of reading by changing the gain of the operational amplifier 26 and variable resistor 32 is adjusted to balance the amplifier 26 so that a stable and consistent output can be represented on the meter M1. In a preferred construction, the variable resistor 32 would be a reverse log type potentiometer. The output signal of the transistor amplifier from transistor TR3 is supplied to the meter M1 where it is displayed.

On the meter M1 is a particular set point and the value of potentiometer section P1A is set by rotating the control associated with potentiometer P1 so that the needle of the meter M1 points at a particular set point. As the resistance of the living body changes. the potentiometer P1 is turned so as to increase or reduce the resistance of potentiometer section P1A to maintain the needle of M1 pointed at the particular set point.

Furthermore, during display on the meter M1 of the resistance of the living body certain sudden or erratic motions of the needle may occur. It is desirable to be able to determine immediately and instantaneously if these variations are the result of actual changes in the living body or some detect in the device. The switch SW1 together with resistor 4 is provided for this purpose. With the push button switch SW1 in its normal condition the electrodes and the living body are connected to the device when the push button SW1 is depressed, a resistor is connected to the input of the bridge network and the jack J1 is disconnected from the device. If the erratic fluctuations of the needle of the meter M1 continue, then it is immediately apparent to the operator that the device is somehow defective. On the other hand, if the fluctuations in the needle suddenly stop. then the operator knows that the living body is undergoing changes in its resistance which are displayed on the meter M1.

In addition, in some applications it may be desirable to be connect the device to a computer. For this purpose the switches SW2 and SW4 together with the interface 42 are provided. The computer interface 42 is connected to a computer and further comprises itself operational amplifiers, buffers and impedance matching networks required to connect the computer to the output of the operational amplifier 26 and to the base of the transistor TR3 so that the computer cannot only receive data in the form of the output from amplifier 26, but also can supply data in the form of a signal to the base of the transistor TR3.

The charger C1 is connected across battery B1 which can be any conventional rechargeable battery such as a NiCad. To provide power to the analog digital sections, the battery is essentially provided across resistor 104, MOSFET 106 and zenor diode Z1 to ground. The level of the voltage which appears at the cathode of zenor diode Z1 is set by MOSFET 106 which in turn is controlled by the output of operational amplifier 108. In particular the output of operational amplifier 108 is supplied to the gate of MOSFET 106 and as a result the magnitude of the output voltage from operational amplifier 108 sets the resistance of the MOSFET 106. By setting the resistance of MOSFET 106, the voltage drop across the MOSFET 106 can be controlled resulting in control of the voltage at the cathode of zenor diode Z1. The voltage which appears at the cathode of zenor diode Z3 is applied to one end of an input of the operational amplifier and is compared with voltage applied to the other end of the terminal of operational amplifier 108 which is sent by the voltage divides network comprising resistors 110 and 112. With this arrangement a stable voltage can be supplied for powering the analog and digital portions and also for supplying the required voltage to the bridge network. Furthermore, this circuitry allows the battery B1 to be of a voltage substantially higher than the requirements for the circuitry so that as the battery B1 is discharged and the voltage decreases, the device continues to operate efficiently and stably over a wide voltage range for the battery B1. This voltage for the battery B1 is equal to the maximum voltage drop across MOSFET 106 plus the minimum voltage to stably operate the apparatus.

In addition to powering both the analog and digital sections of the device, the battery B1 further powers the operational amplifier 108. In addition, the voltages that appear at the cathode and anode of the zenor diode Z1 are very stable and provide the voltage arms of the bridge network.

In the digital portion of the device, the rotation of the control knob on the potentiometer P1 turns both the potentiometer section P1A and potentiometer section P1B in unison. Since a voltage is applied across the potentiometer P1B the movement of the variable wiper of the potentiometer causes a differing voltage to appear at the input of the comparator 120. This input to the comparator 120 is compared with some other reference value by the comparator 120 and an output signal which is either positive, negative or zero is generated by the comparator based on whether the input voltage from potentiometer P1B is either greater than, less than or equal to, respectively, the reference voltage. The output of the comparator 120 is supplied to UP/DOWN counter 122 and the UP/DOWN counter 122 counts up based upon a positive signal, down upon a negative signal and makes no change upon the application of a zero. The up count of the UP/DOWN counter 122 is supplied to the up count input of counter 124 which essentially accumulates the count. Accordingly, the number contained in the counter 124 is accumulative count and is indicative of the amount that potentiometer P1B has been turned in total. Counter 124 supplies an output signal to a digital display driver 128 which in turn drives a digital display 130 which in fact indicates the total accumulative count to the operator.

The up and down count outputs of UP/DOWN counter 122 are supplied to respectively the up and down count inputs of counter 126. Accordingly, counter 126 counts up and down in accordance with UP/DOWN counter 122. As a result, the count contained in counter 126 is indicative of the position of the wiper of potentiometer P1B. This count is supplied to digital display driver 132 which in turn drives a digital display 134. In addition, the output of counter 126 is supplied to a D/A converter 136 which converts the count into an analog voltage. This analog voltage is supplied to the reference input of the comparator 120 and it is compared with the voltage from the potentiometer section P1B. As a result, a closed loop feedback system is provided for controlling the accuracy of the count.

Since the total accumulative count is displayed by the digital display 130 and a count indicative of the position of the wiper of potentiometer P1B is displayed by digital display 134, an accurate indication of the position of the controls and of the operation of the device can be given to the operator. It should also be apparent that while the digital display 134 is indicative of the position of potentiometer P1B. It also indicates the position of potentiometer P1A since they are ganged together on the potentiometer P1.

In addition, when using the above device and when desiring to conduct another session on either same living body or another living body, a reset signal can be supplied to the UP/DOWN counter 122 and the counters 124 and 126 to reset them back to zero. After this is done, the entire process can be repeated again.

Furthermore, if one desires to record the output signal from the operational amplifier 26 on a computer, the switch SW2 is set in the open position and the switch SW4 is closed. In this way the output signal from the operational amplifier 26 can be fed through the interface 42 to a computer for recording an analysis. If one desires to display the previously recorded output of the amplifier 26 on the meter M1 of the device, the switch SW2 is set in the position to connect the interface 42 to the base of the transistor TR3. Also, the switch SW4 is opened. In this way, an output signal from a computer can be applied to the base of the transistor TR3 and displayed on the meter M1. It should also be apparent that if the computer is a digital computer, analog to digital and digital to analog circuits would be utilized in the interface 42 to make the appropriate conversions of the output signal from the amplifier 26 and the output from the digital computer.

While the circuits of the digital portion have been shown as black boxes, it should be apparent to one skilled in the art that these circuits can be implemented with standard and well known digital devices which exist in the prior art; however, it is preferable that the digital devices selected to perform these functions should be low in power consumption and preferably of CMOS type. In addition, and as previously pointed out, the digital displays 130 and 134 can be any type of digital displays but it is preferably that the digital displays are low power consumption such as liquid crystal displays.

Figure 3:
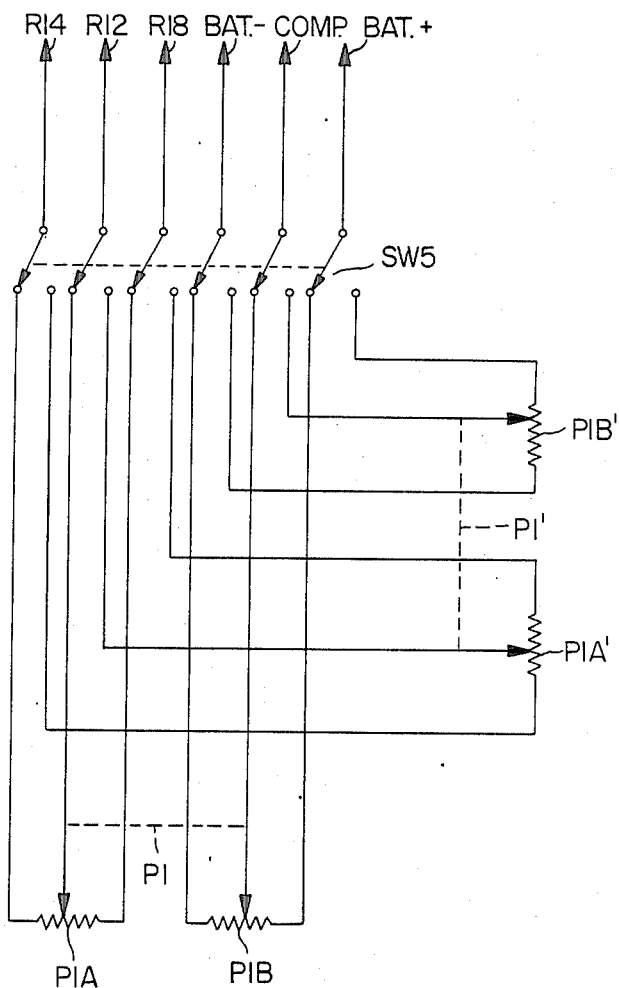
FIG. 3 is a modification of the diagrams shown in FIGS. 1 and 2 at the dotted line 3—3.

Referring to FIG. 3 shown therein is a modification of the diagrams of FIGS. 1 and 2 along the dotted line 3—3. In particular, the connections which are normally applied to the ganged potentiometer P1 are made to the fixed switch contact of multi-pole, two position, slide switch SW5. The contacts of one position of the multi-pole two position switch SW5 are connected directly to variable resistors P1B and P1A of ganged potentiometer P1. This ganged potentiometer P1 is located in the device in the same manner as in the construction of FIG. 1, but is connected to the circuitry via the multi-pole, two position, slide switch SW5. A remote ganged potentiometer P1' which consists of potentiometers P1B' and P1A' is connected to the contacts of the other position of the multi pole, two position, slide switch SW5. In this way, a remote ganged potentiometer P1' could be connected to the device via cabling and a plug can be selected to control the device via the multi-pole, two position, slide switch SW5.

It should be apparent that the switches in the device which are shown in FIGS. 1 and 3 could be implemented electronically using transistors, gate circuits, relays and integrated circuits.

It should further be apparent to those skilled in the art that the above-described embodiment is merely illustrative of but one of the many possible embodiments which represent the applications of the principles of the present invention. Numerous and varied other arrangements can be readily devised by those skilled in the art without departing from the spirit and scope of the invention.

We claim:

1. A device for measuring and indicating changes in a living body comprising:
    an analog portion, said analog portion comprising a bridge network having on one side thereof a first resistance arm connected in series with a second resistance arm, and on another side thereof a first voltage arm connected in series with a second voltage arm, there being connected in series between the junction of the first and second resistance arms and the first and second voltage arms an amplifier circuit and current indicating means indicating changes in balance of said bridge network, two electrodes to be connected to a living body, one of said electrodes being electrically connected to a terminal of one of said resistance arms, whereby said living body is adapted to be connected across said one of said resistance arms, a range control device comprising a first gang of a double ganged potentiometer coupled in parallel with said first voltage arm, said first gang of said double ganged potentiometer having a sliding contact electrically connected to a terminal of said first voltage arm, the other of said electrodes being electrically connected to said sliding contact, a variable resistor electrically coupled to said one or said electrodes which is electrically connected to said terminal of one of said resistance arms and the junction of the first and second resistance arms for enabling a balance to be established in an initial setting of said bridge network, said amplifier circuit comprising a first transistor emitter follower, an operational amplifier and third transistor connected to the output of said emitter follower with one input of said operational amplifier being connected to the emitter of said first transistor and the output of the operational amplifier being connected to a base of said third transistor and a collector of the third transistor forming an output of said transistorized amplifier circuit, a variable resistive feedback branch connecting the output of the operational amplifier to another input of the operational amplifier;
    a digital portion, said digital portion comprising a comparator, a second gang of said double ganged potentiometer, a sliding contact of said second gang being coupled to one input of said comparator, an UP/DOWN counter coupled to the output of the comparator, a first counter coupled to the up count output of said UP/DOWN counter, a first digital display driver coupled to the output of the first counter, a first digital display driven by said first digital display driver for displaying the total rotation of said second gang of said double ganged potentiometer in one direction, a second counter coupled to both the up and down count outputs of the UP/DOWN counter, a second digital display driver coupled to the output of the second counter, a digital to analog converter having an input coupled to the output of said second counter and an output coupled to another input of said comparator for supplying a comparison value for said comparator, and a second digital display driven by said second digital display driver for displaying a present position of the second gang of said double ganged potentiometer; and
    a source of power for supplying power to said analog and digital portions and for setting stable voltage levels as said first and second voltage arms of said bridge network, said source of power comprising a single battery, an operational amplifier coupled to said battery and a voltage controlled variable resistance means coupled to said battery and controlled by an output voltage of said operational amplifier.

2. A device for measuring and indicating changes in the resistance of a living body according to claim 1, wherein said voltage controlled variable resistance means comprises a MOSFET whose gate is coupled to the output of the operational amplifier.

3. A device for measuring and indicating changes in the resistance of a living body according to claim 2, further comprising a switch means for disconnecting said electrodes from said bridge network and for substituting in their stead a fixed resistor whereby it can be determined if fluctuations on the current indicating means are as a result of changes in the resistance of a living body or a defect in said device for measuring and indicating changes in the resistance of a living body.

4. A device for measuring and indicating changes in the resistance of a living body according to claim 3, further comprising switch means and interface means coupled to said amplifier circuit whereby the changes in the resistance of the living body can be recorded in a computer and the recorded changes could be displayed on the meter.

5. A device for measuring and indicating changes in resistance of a living body according to claim 4, further comprising switch means provided between said first gang of said double ganged potentiometer and the remainder of the analog portion and between the second gang of the double ganged potentiometer and the remainder of the digital portion and a remotely located second double ganged potentiometer connected to said switch means such that said analog and digital portions can alternately be connected to said double ganged potentiometer and said second double ganged potentiometer.

6. A device for measuring and indicating changes in resistance of a living body according to claim 3, wherein said transistors of said amplifier circuit are made of silicon.

7. A device for measuring and indicating changes in the resistance of a living body according to claim 2, further comprising a battery charger provided across the single battery.

* * * * *